United States Patent [19]
Klinger et al.

[11] 4,056,974
[45] Nov. 8, 1977

[54] METHOD AND HYDRAULIC TESTING APPARATUS FOR PERFORMING RESONANCE TESTS

[75] Inventors: Friedrich Klinger, Garmisch-Partenkirchen; Josef Beran, Ober-Ramstadt; Jan Brezina, Darmstadt, all of Germany

[73] Assignee: Carl Schenck AG, Darmstadt, Germany

[21] Appl. No.: 686,712

[22] Filed: May 17, 1976

[30] Foreign Application Priority Data
May 23, 1975 Germany .............. 2522890

[51] Int. Cl.² ............................................ G01N 3/32
[52] U.S. Cl. ............................................ 73/92; 73/579
[58] Field of Search ............. 73/92, 67.2, 67.3, 91

[56] References Cited
U.S. PATENT DOCUMENTS

| | | | |
|---|---|---|---|
| 2,530,483 | 11/1950 | Russenberger | 73/92 |
| 3,442,120 | 5/1969 | Russenberger et al. | 73/92 |
| 3,508,159 | 4/1970 | Marpe | 73/91 |
| 3,572,097 | 3/1971 | Kleesattel | 73/67.2 |
| 3,664,179 | 5/1972 | Danko et al. | 73/67.2 |

Primary Examiner—Richard C. Queisser
Assistant Examiner—Anthony V. Ciarlante
Attorney, Agent, or Firm—W. G. Fasse; W. W. Roberts

[57] ABSTRACT

Materials, or structural components are tested under resonance conditions by means of a pressure operated load mechanism controlled by a servo-hydraulic control unit. The pressure medium is part of the oscillating system. The spring rate or stiffness of the pressure medium is adjusted relative to the spring rate of the test sample, or rather relative to the spring rate of the entire oscillating system in such a manner that the maximum pressure occurring at resonance operation corresponds as close as possible to the rated supply pressure of the system. The load mechanism comprises a single cylinder for producing dynamic loads for the resonance operation and also static loads of substantially the same size as said dynamic loads.

14 Claims, 6 Drawing Figures

METHOD AND HYDRAULIC TESTING APPARATUS FOR PERFORMING RESONANCE TESTS

BACKGROUND OF THE INVENTION

The present invention relates to a method and apparatus for resonance testing of materials and structural components. The test body or sample and certain components of the testing apparatus form a system capable of oscillating and the system is driven or excited in resonance. The testing apparatus comprises a load mechanism operated by a pressure medium and a servo-hydraulic control unit operatively connected to the load mechanism.

Resonance testing of materials and structural components is employed for many purposes, especially for material strength testing and durability or useful life testing. Such resonance testing methods take advantage of the fact that strong forces or rather dynamic loads may be generated by a relatively low energy input in a spring mass system driven at its resonance frequency, whereby the forces are applied as testing loads to the test sample or body. The test sample constitutes the spring of the oscillatory system, which spring must take up the forces occurring when the system oscillates. The mass of the oscillatory system comprises, for example, the piston of a hydraulic load mechanism, the piston rod, the clamping means for the testing sample, and possibly also auxiliary masses participating in the oscillation. When such a spring mass system is operated at its resonance frequency, it is merely necessary to supply to the system the power required to make up for the power losses resulting from the damping caused by the test sample and other friction and damping losses of the oscillatory system to maintain the oscillation. Further, it is possible to control the force applied to the test sample by varying the power supplied to the system to thereby vary the oscillation amplitude. The resonance frequency f of such a system may be ascertained, as is well known, from the spring rate and from the mass of the system:

$$(f = \frac{1}{2\pi} \sqrt{\frac{c}{m}})$$

By varying the spring rate $c$ and/or the mass $m$ it is possible to vary the resonance frequency $f$ of the system.

German Patent Publication No. 2,213,736 describes a method for performing resonance testing with the aid of a material testing machine comprising a main piston cylinder arrangement for producing static or slowly variable loads and a further, smaller piston cylinder arrangement connected to the main cylinder for producing dynamic loads at resonance. The main cylinder produces substantially a mean force or a preload static force, whereas the second cylinder acts as an exciter for the dynamic alternating load. The known apparatus also comprises hydraulic servo-valves for the control of the pressure medium supplied to the two cylinders as well as electrical control and regulating devices. The servo-valves permit a very rapid and exact control of the pressure medium supply and removal from the load cylinders. Accordingly, a respectively rapid and precise control of the load is accomplished through these valves. The known apparatus further includes pressure storage means arranged for cooperation with the main cylinder providing the static load. These pressure storage means act as equalization or compensation containers for the pressure medium. These pressure medium storage containers receive or supply the pressure medium quantities which are moved along as a result of the oscillating movements of the static load applying piston, when an additional preload is applied through the static load applying, so called preload piston during resonance operation. Generally, such a known apparatus may be used to generate static loads as well as variable loads having any desired load characteristic, for example, for random testing. The apparatus may also be used to apply dynamic loads in the resonance operation.

The oscillatory system of the apparatus according to said German Patent Publication comprises the test sample or body, a mass secured to the piston rod of the main cylinder, as well as the pistons and the piston rods of the main piston cylinder arrangement and of the exciter piston cylinder arrangement. The remainder of the known testing machine is substantially rigid. For producing the oscillatory load, the double-acting exciter cylinder is supplied with pressure medium through a hydraulic servo-valve in such a manner that both cylinder chambers receive the pressure medium in an alternating manner. Thus, each stroke movement of the piston supplies an exciting energy to the oscillating system through the piston of the exciter cylinder. The direction of the force applied to the pressure medium and the direction of the piston are respectively the same. Thus, this excitation or rather repeated excitation maintains the once started oscillation. The desired load may be adjusted by adjusting the oscillation amplitude at a respective control and regulating unit.

When the exciter piston is at its upper or at its lower return point, the pressure in the chambers of the exciter cylinder is rather small, because the pressure ratios in the chambers are reversed as a result of each piston stroke. However, the supply pressure of the pressure medium supplied for the excitation is very high. As a result, respective throttle losses must be taken into account in the pressure medium supply. Therefore, the exciter cylinder for producing the dynamic load is dimensioned as small as possible so that only small pressure medium quantities are required and that high testing frequencies may be achieved.

The direct control of the pressure medium in the preload or main cylinder during resonance operation would require high driving powers for the hydraulic drive means due to the large pressure medium quantities. Further, large valve units with large flow areas would be required for the same reason. These characteristics of the prior art apparatus thus have substantial control and regulating disadvantages. The pressure medium quantities necessary for the operation of a hydraulic cylinder may be roughly circulated from the oscillation amplitude or the piston stroke and the testing frequency.

Another disadvantage of the known apparatus is seen in that in addition to the main piston cylinder arrangement, an exciter piston cylinder arrangement is required together with the hydraulic and electric control means for producing the dynamic loads including switching devices for the several types of operation as well as pressure medium storage means which need to be switched on and off. These additional structural requirements result in a complicated structure, which for that reason alone is rather expensive and which makes the testing procedure rather involved.

Normally, in connection with hydraulic testing procedures, it is assumed that the employed pressure medium is incompressible for calculating purposes. Stated differently, the pressure medium is assumed to be rigid and not elastic, although in fact it has a certain elasticity. Generally, the elasticity of the pressure medium is undesirable and it has disadvantageous effects, especially with regard to the control and regulating devices. Thus, the elasticity of the pressure medium has hardly been utilized heretofore. However, it is, for example, known to use the elastic pressure medium as a counter spring for oscillating masses.

OBJECTS OF THE INVENTION

In view of the foregoing, it is the aim of the invention to achieve the following objects, singly or in combination:

to eliminate the drawbacks of the prior art by means of a method and apparatus for resonance testing which does not require a separate exciting cylinder piston arrangement, in other words, the arrangement shall be such that the excitation of the dynamic load may be achieved in a single main cylinder;

to provide a method and apparatus for resonance testing which has an operational range similar to that of the prior art, however, without the use of a separate excitation piston cylinder arrangement;

to use only small pressure medium quantities for the excitation in the resonance operation;

to employ testing forces or loads which are substantially the same in the resonance operation as in the static operation;

to employ in the resonance operation a preload or static load without the need for a pressure storage device;

to provide a simple and economical method and apparatus for the dynamic testing of materials as well as structural elements in a resonance operation, whereby the low friction and damping losses are to maintain the power input small as compared to conventional methods, and whereby the efficiency is correspondingly high while simultaneously providing an operational range practically as wide as heretofore;

to avoid the need for additional pressure equalization chambers;

to utilize the load piston cylinder arrangement simultaneously for maintaining static preloads as well as dynamic loads in a resonance operation;

to vary the spring rate or stiffness of the pressure medium in accordance with the spring rate of the material or structural element to be tested; and to use a single hydraulic servo-valve for the simultaneous production of static preloads and dynamic loads with the single piston cylinder arrangement of the load applying mechanism.

SUMMARY OF THE INVENTION

According to the invention there is provided a method for resonance testing materials and structural elements, wherein the test sample forms part of a vibratory system in a testing apparatus including a pressure medium operated load mechanism controlled by a servo-hydraulic control unit, wherein the pressure medium constitutes an elastic member or so called oil spring of the oscillatory system, whereby the spring rate of the pressure medium is adjusted to the spring rate of the test sample or to the spring rate of the entire oscillatory system, as well as to the masses thereof in such a manner that the maximum pressures occurring in the hydraulic load mechanism during resonance operation correspond as closely as possible to the rated or permissible supply pressure of the system.

it is an advantage of the foregoing method that the energy input is smaller than heretofore due to the low friction and damping losses, whereby the efficiency of the testing procedure is correspondingly high while simultaneously permitting a substantially unchanged width in the operational testing range.

The energy for exciting the oscillatory system in resonance is supplied according to the invention by applying and withdrawing pressure medium to the elastic medium in the load mechanism, whereby preferably servo-hydraulic valve means are employed. Preferably, the pressure medium is applied when the pressure in the cylinder is high and withdrawn when the pressure in the cylinder is low, because thereby an especially efficient utilization of the energy in the applied pressure medium is achieved, because the throttle losses which would otherwise result, due to a large pressure drop between the supply pressure in the pressure medium supply and the cylinder pressure, are substantially avoided. An apparatus according to the invention for performing the foregoing method comprises a pressure medium operated load mechanism for applying a load to the test sample and a control unit, wherein the load mechanism comprises a single load piston cylinder arrangement for producing of dynamic loads in the resonance operation as well as static loads having substantially the same size. By producing both types of loads with the same single piston cylinder arrangement, the advantage is achieved that the entire structure is substantially simplified as compared to prior art devices of this type employing two load piston cylinder arrangements. The simplification results from the elimination of the additional exciter piston cylinder arrangement with the respective electrical and hydraulic control mechanism required for the exciter piston cylinder arrangement.

In a preferred embodiments, the static preload and the dynamic loads in the resonance operation may be applied simultaneously. This has the advantage that the single piston cylinder arrangement is capable to service substantially the same operational range as prior art two cylinder testing machines. In addition, several measuring and control problems are obviated, which heretofore resulted from the use of two load cylinders and from the use of storage systems, which were required heretofore for the application of static preloads.

BRIEF FIGURE DESCRIPTION

In order that the invention may be clearly understood, it will now be described, by way of example, with reference to the accompanying drawings, wherein.

DETAILED DESCRIPTION OF PREFERRED EXAMPLE EMBODIMENTS

Figure 1:
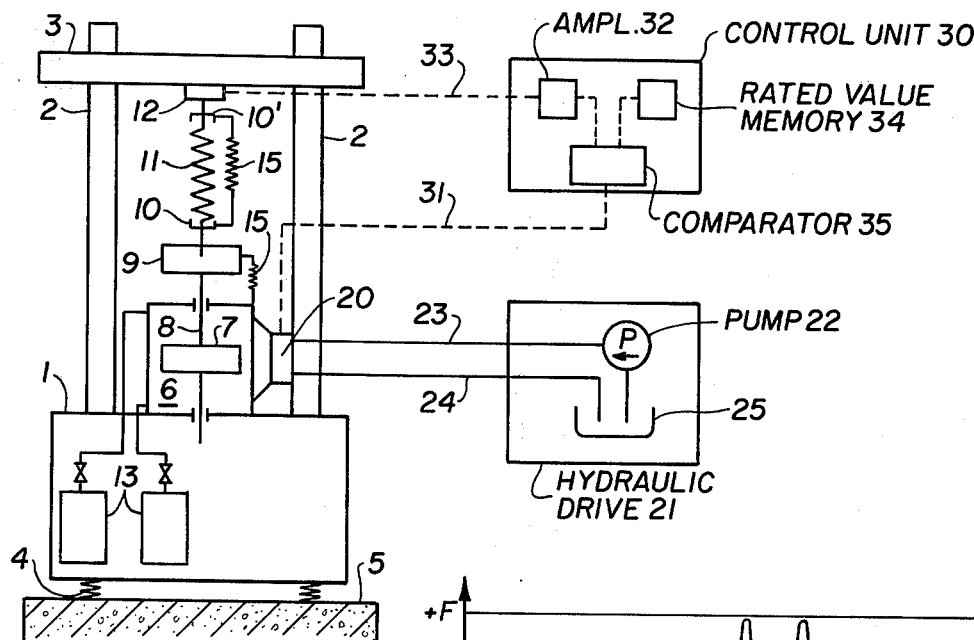
FIG. 1 is a schematic illustration of a hydraulic testing apparatus according to the invention.

FIG. 1 shows the hydraulic testing machine according to the invention in a schematic manner. The machine frame comprises a base 1 supporting upright columns 2, which are interconnected by cross beam 3. The machine frame is supported on the floor 5 by elastically yielding members 4, such as springs or the like. A testing cylinder 6 is secured to the base 1. A load piston 7 is movable up and down in the cylinder 6 and the piston rod 8 extends out of the cylinder 6. An auxiliary mass 9 is secured to the piston rod 8. Such mass may vary in size or may be omitted altogether. A lower chucking head 10 is secured to the upper end of the piston rod. A further chucking head 10' is supported by the cross beam 3 in such a manner that a load cell 12 is enabled to register the forces applied to the test sample 11, which is held by the two chucking heads 10 and 10'. The test sample 11 is illustrated as an elastic body. Preferably, the chucking head 10' will be connected to the cross beams 3 through the load cell 12.

The invention is not limited to the specific arrangement just described. For example, the load cylinder could be secured to the cross beam 3 and the load cell 12 could be secured to the base 1.

The test sample 11 substantially forms with the chucking heads 10, 10', with the auxiliary mass 9, the piston rod 8 and the piston 7 as well as with the pressure medium in the load cylinder 6 and in the pressure medium containers 13, the oscillatory system. If necessary, further elasticities may have to be taken into account in addition to those of the test sample 11 and the pressure medium.

Preferably, but not necessarily, the load cylinder 6 may be connected through respective shut-off valves to pressure medium containers 13 by means of which it is possible to vary the spring rate of the elastic medium in the load cylinder 6 in a wide range. The volume of the containers 13 may be variable continuously or in steps, for example, by means of air bubbles or the like. Further, for varying the spring rate of the spring mass system, as just described, additional springs 15 may be provided between the chucking heads, 10, 10', between the auxiliary mass 9 and the base frame 1, or between the test sample 11 and the chucking heads 10. In other words, additional springs could be connected in series or in parallel to the test sample 11.

The load cylinder 6 is controlled by a servo-valve 20 which in turn is connected through an electrical conductor means 31 to a control unit, which in turn is connected through electrical conductor means 33 to the load cell 12. The servo-valve 20 is connected through hydraulic conduits 23, 24 to a hydraulic drive 21, whereby the servo valve 20 admits the pressure medium supplied by the high pressure pump 22 through the conduit 23 to the cylinder chambers of the load cylinder 6. The return flow is accomplished through the valve 20 and the conduit 24 into a sump 25.

The control unit 30 comprises a measuring amplifier 32 connected to the load cell 12 through the electrical conductor 33. The amplifier 32 amplifies the signals from the load cell 12 and supplies these signals to a comparator 35, which also receives rated value signals from a rated value memory 34. The output of the comparator 35 is connected through the electrical conductor 31 to the servo-valve 20 to control the latter. The amplifier, the rated value memory, and the comparator are conventional electrical circuit arrangements. Thus, the control unit 30 permits the control of the servo-valve 20 in such a manner that static loads, quasi-static loads and dynamic loads may be applied to the test sample 11 by means of the single cylinder arrangement 6. The working frequency of the servo-valve 20 may, for example, be at several hundred Hz.

When the testing involves static or quasi-static, that is, slowly changing loads applied to the test sample, the control unit 30 automatically adjusts the valve 20 in accordance with the values stored in the rated value memory 34. The values coming from the load cell 12 are continuously compared in the comparator 35 with the rated values and the comparator 35 forms a difference value between the measured value and the rated value to produce control signals for the servo-valve 20, which thus regulates the load cylinder in accordance with the rated value.

In order to test a test sample in a resonance testing operation, it is necessary to first ascertain its spring rate. Since the load to be applied to the test sample is known, it is then possible upon ascertaining the spring rate of the test sample to calculate the spring deflection or rather the deflection amplitude in the load mechanism, as well as the required spring deflection and the spring rate of the elastic pressure medium in the load cylinder 6. As mentioned, the pressure in the pressure medium resulting from maximum compression shall be as close as possible to the permissible supply pressure of the load mechanism. However, the pressure medium shall not be subjected to a complete pressure release at the point of maximum relaxation. The resonance frequency may be ascertained on the basis of the above formula from the spring rate of the test sample 11 and from the spring rate of the elastic pressure medium as well as from the elasticities of further elements forming part of the oscillatory system and from the masses of such system.

The control unit 30 is then adjusted to operate the servo-valve 20 at the calculated resonance frequency, whereby pressure medium is periodically applied and removed from the load cylinder 6 at this frequency. If the actual resonance frequency of the system should not precisely correspond to the resonance frequency as calculated, it is possible to adjust the exciter frequency of the servo-valve 20 by trial and error until the optimum conditions are attained. Such regulation of the servo-valve 20 can also be performed automatically by means well known in the art.

When the oscillatory spring mass system is excited by means of the servo-valve 20, through the oil spring in the resonance frequency of the system, the latter begins to oscillate. The oscillating amplitude can be adjusted by controlling the power of the excitation within the above mentioned limits, namely, that the maximum pressure shall not be larger than the supply pressure and that the minimum pressure shall be larger than zero. This control is accomplished by correspondingly opening the servo-valve 20.

The exciter amplitude and thus the pressure medium volume required for the excitation in resonance for each oscillation is smaller than the pressure medium volume which can be calculated from the oscillation amplitude of the load mechanism. More specifically, the first mentioned exciter pressure medium volume is smaller than the last mentioned load mechanism pressure medium volume by the amplification factor at resonance operation. Moreover, the pressure medium is supplied to the cylinder at high cylinder pressure, that is when the oil spring is heavily biased, and the pressure medium is removed from the cylinder 6 when the oil spring is less strongly biased. This feature has the advantage that only small throttle losses occur during the pressure medium supply because of the small pressure differentials between the supply pressure and the cylinder pressure, whereby a high efficiency is achieved according to the invention. As a matter of fact, the small pressure medium quantities required for maintaining the oscillation make it possible at all to use large load cylinders directly for the excitation of the oscillation.

Figure 4:
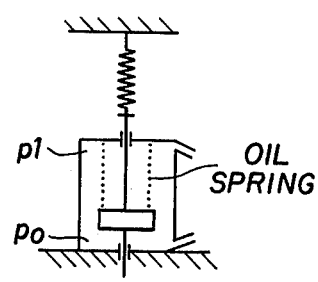
FIG. 4 shows a piston cylinder arrangement wherein the piston is subjected to loads on one side only.

The spring rate of the elastic pressure medium can be adapted in different ways to the spring rate of the test sample 11. If the load piston 7 is centrally located in the load cylinder 6, the two oil springs in the two cylinder chambers above and below the piston 7 have the same spring rate. The resultant spring rate corresponds to the sum of the individual spring rates, whereby the resultant spring rates can be varied by shifting the load piston 7 from the center position into any position along the length of the cylinder 6. The oil spring thus becomes harder and the resultant or total spring rate for both cylinder chambers becomes larger. If the load cylinder is supplied with pressure medium on one side only for a pure tensile load or for a pure pressure load, the piston 7 may be brought into one of its end positions, as shown in FIG. 4. In this manner, the pressure medium volume in the cylinder chamber is increased and the oil spring becomes softer, whereby the spring rate becomes smaller.

If the desired range of adjustment of the spring rate of the oil spring cannot be accomplished solely by the pressure medium volume in the cylinder 6, it is possible to use the auxiliary containers 13, whereby an adaptation or adjustment of the spring rate of the elastic pressure medium is possible in a wide range.

Figure 2:
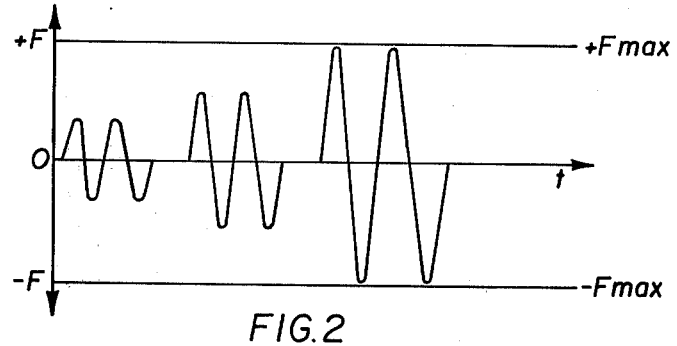
FIG. 2 is a load diagram for dynamic loads which may be applied by means of the present apparatus.

In the present specification it was so far assumed that the test sample 11 is not subjected to any load at the beginning of the resonance testing. Thus, when the oil spring is adjusted, the pressures in the two chambers of cylinder 6 must initially be the same when pressure is supplied to both cylinder chambers, whereby the compression of the elastic pressure medium in the chambers may be different depending on the chamber volume. When load is applied to the test sample 11 in the resonance operation, the load is a tension-pressure alternating load, which varies about the time axis in a sine fashion. FIG. 2 illustrates the load characteristics for three loads of different sizes showing the load forces F as a function of time $t$. $+Fmax$ designates the maximum tension force and $-Fmax$ designates the maximum pressure force. These maximum values correspond substantially to the peak testing forces that may be achieved at static loads.

In addition to the oscillating load, the load cylinder may be subjected to a static load, which may either be a tension load or a pressure load. To this end the chambers of the load cylinder 6 are subjected to different pressures through the servo-valve 20 prior to the begin of the testing in such a manner that the desired preload or static load is obtained. The thus biased system may be excited at its resonance frequency in the same manner as the system without the static bias load. The excitation for the dynamic load is also applied through the servo-valve 20, which oscillates at the resonance frequency about its center position when no static load is applied and about a position displaced from the center position when a static load and a dynamic load are applied simultaneously. Thus, the static load may be maintained also at resonance operation. The adjustment of the servo-valve 20 is accomplished through the control unit 30 by well known means.

Where the testing is done with a biasing static load and the dynamic load, it is necessary that the maximum pressure occurring in the cylinder chamber with the larger biasing load and comprising a bias component as well as a dynamic component does not exceed the supply pressure. Simultaneously the pressure in the cylinder chamber with the lower biasing must not fall to zero value.

Figure 4A:
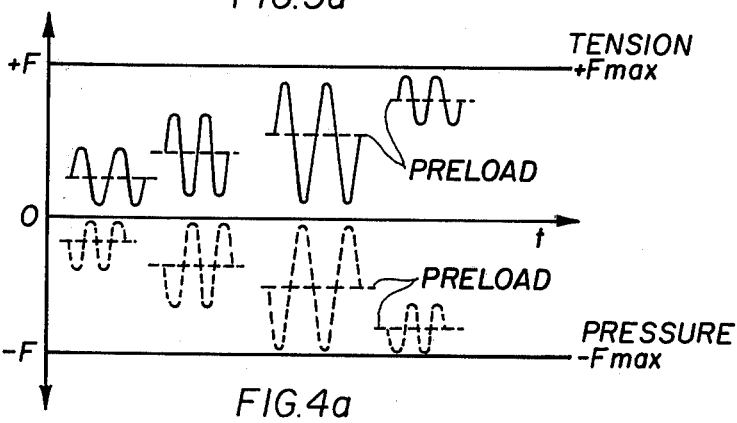
FIG. 4a shows a load diagram for the arrangement of FIG. 4.

It is especially advantageous to supply pressure to one cylinder chamber only for the pressure testing or for pure tension testing. In this instance a very low oil consumption is achieved and the possibilities given to vary the stiffness of the oil spring by the position of the piston 7 in the cylinder 6 as best seen in FIG. 4, wherein a tension load is illustrated with the static pressure $p1$. The lower cylinder chamber is vented to atmospheric pressure $po$. On the other hand where a pressure load is applied the static pressure $p1$ will be present in the chamber below the piston and the upper chamber will be vented to atmospheric pressure $po$. FIG. 4a illustrates the dynamic tension loads in full lines relative to four different static bias loads and dashed lines indicate similarly four different dynamic pressure loads relative to four different static loads.

Figure 3:
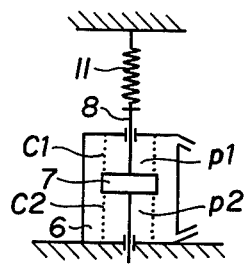
FIG. 3 illustrates in a simplified manner a hydraulic load cylinder for resonance testing, whereby the piston may be subjected to loads on both sides.
Figure 3A:
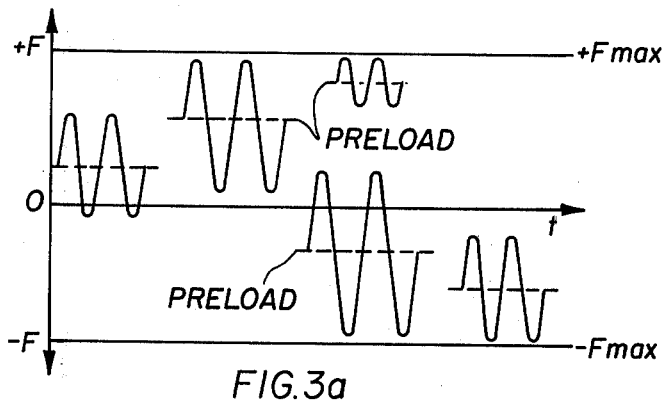
FIG. 3a is a load diagram for the embodiment of FIG. 3.

FIG. 3 illustrates in simplified form the cylinder 6 and the piston 7 whereby the latter is in an intermediate position, the piston rod 8 is connected to a test sample 11. The oil springs in the two cylinder chambers above and below the piston 7 are symbolically illustrated by coil springs having the spring rates or constants $c1$ and $c2$. The total or resulting spring constant of the oil is $c_{oil} = c1 + c2$. When the preload pressure $p1$ in the upper chamber is larger than the preload pressure $p2$ in the lower chamber, the load will be a tension load and a pressure load is accomplished when the pressure $p2$ is larger than the pressure $p1$. FIG. 3a shows the testing forces F as a function of time. Three different dynamic tension loads are illustrated as a function of time $t$ relative to three different static loads indicated by dashed horizontal lines. The three dashed horizontal lines above the time axis represent a static tension load and the two horizontal lines below the time axis represent two different static pressure loads superimposed with different dynamic pressure loads. The static load corresponds to the mean pressure in the cylinder chamber which is subjected to pressure. The sine curves illustrate the dynamic loads with different force amplitudes. The maximum pressure force corresponds to $-Fmax$ and the maximum tension force corresponds to $+Fmax$.

The above described embodiments of FIGS. 3 and 4 illustrate the advantage achieved by the invention that the single cylinder piston arrangement can be used for the simultaneous application of a dynamic and a static load, whereby the cylinder chambers may be subjected to different pressures or one cylinder chamber may be vented to atmospheric pressure. This has the advantage that pressure compensation chambers or pressure storage containers can be avoided. If only one cylinder chamber is employed, it is possible to test the sample with pressure only or with tension only, whereby the adjustable preloads or rather their amplitudes are larger than the amplitudes where both cylinder chambers are subjected to pressure. Another advantage of the arrangement of FIG. 4 is seen in that the stiffness of the oil spring can be varied in a very wide range.

In the light of the above disclosure, it will be appreciated that in the apparatus according to the invention the stiffness or spring rate of the pressure medium can be varied in a wide range and is thus easily adapted to different spring rates of different test samples. Thus, the testing frequency and the testing amplitude may accordingly be varied.

An especially wide range of variation for the stiffness or spring rate of the pressure medium may be accomplished by the use of additional containers 13 as shown in FIG. 1. Another variation possibility resides in the starting position of the piston 7 relative to its center position as described above. The positioning of the piston 7 is an especially simple expedient for the control or varying of the stiffness of the oil spring.

Similarly, it is a simple expedient to place the movable member of the hydraulic servo-valve 20 out of its center position where the testing employs dynamic and static loads simultaneously.

Although the invention has been described with reference to specific example embodiments, it is to be understood, that it is intended to cover all modifications and equivalents within the scope of the appended claims.

We claim:

1. In a method for resonance testing of materials and structural elements in which a test sample constitutes with the members of a testing apparatus a unit including a load mechanism with a single cylinder piston arrangement forming two cylindrical chambers and a pressure medium in said load mechanism, and an oscillatory system driven at resonance, the improvement comprising the steps of incorporating said pressure medium in the load mechanism as an elastic element of said oscillatory system, adjusting the spring rate of the pressure medium relative to the spring rate of the test sample or relative to the spring rate of the entire oscillatory system of the testing apparatus, further adjusting the spring rate of the pressure medium also relative to the mass of said oscillatory system, and supplying the pressure medium to said single cylinder piston arrangement for exciting the oscillation of said oscillatory system, at high pressure in said single cylinder piston arrangement, whereby any pressure difference between supply pressure of the system and the pressure in the single cylinder piston arrangement at the time of pressure supply is minimized.

2. The method according to claim 1, wherein the power for exciting the oscillatory system at resonance is applied by supplying and removing pressure medium to and from said pressure medium in the load mechanism which forms an elastic element of the oscillatory system.

3. The method according to claim 2, wherein the pressure medium is supplied to said elastic element through servo hydraulic valve means.

4. The method according to claim 2, wherein the pressure medium for exciting the oscillation is removed at low pressure in said single cylinder piston arrangement of said load mechanism.

5. The method according to claim 1, further comprising employing said load mechanism, which is excited for the generation of oscillations, simultaneously for producing a preload and a dynamic alternating load.

6. The method according to claim 5, comprising supplying pressure medium to the two cylinder chambers of the cylinder of the load mechanism, in an uneven manner for producing a pre-load.

7. The method according to claim 1, wherein only one chamber of said single cylinder piston arrangement of the load mechanism is supplied with pressure medium whereas the second chamber is vented to atmospheric pressure.

8. In a hydraulic testing apparatus for testing test samples at resonance, comprising a hydraulically operated load mechanism including an oscillatory system with a single cylinder piston arrangement having a pressure medium therein for applying to a test sample dynamic loads in a resonance operation as well as preloads, and hydraulic control valve means operatively connected to said single cylinder piston arrangement, the improvement comprising a hydraulic control unit operatively connected to said control valve means and responsive to the applied testing forces, said test sample and said pressure medium in said single cylinder piston arrangement each forming an active elastic spring element of said oscillatory system, said hydraulic control unit operating said control valve in such a manner that oscillation exciting pressure is supplied to the oscillatory system at high pressure in said single cylinder piston arrangement.

9. The hydraulic testing apparatus according to claim 8, wherein said single cylinder piston arrangement is adapted to simultaneously apply pre-load and dynamic loads to said test sample at resonance operation.

10. The hydraulic testing apparatus according to claim 8, wherein said active elastic spring element pressure medium in said oscillatory system has a variable spring rate.

11. The hydraulic testing apparatus according to claim 8, further comprising pressure container means and means operatively connecting said pressure container means to said single cylinder whereby the pressure medium volume of the load mechanism is variable in a wide range.

12. The hydraulic testing apparatus according to claim 8, further comprising additional spring means for varying the spring rate of the oscillatory system.

13. The hydraulic testing apparatus according to claim 8, further comprising means for adjusting the piston of the single cylinder piston arrangement into any desired starting position within said cylinder.

14. The hydraulic testing apparatus according to claim 8, wherein said hydraulic control valve for the control of the cylinder is so controlled that it oscillates about a position which is displaced relative to its center position.

* * * * *